(12) United States Patent
Mazur et al.

(10) Patent No.: US 7,715,003 B2
(45) Date of Patent: May 11, 2010

(54) METALIZED SEMICONDUCTOR SUBSTRATES FOR RAMAN SPECTROSCOPY

(75) Inventors: Eric Mazur, Concord, MA (US); Eric Diebold, Boston, MA (US); Steven Ebstein, Newton, MA (US)

(73) Assignee: President & Fellows of Harvard College, Cambridge, MA (US)

( * ) Notice: Subject to any disclaimer, the term of this patent is extended or adjusted under 35 U.S.C. 154(b) by 103 days.

(21) Appl. No.: 12/017,720

(22) Filed: Jan. 22, 2008
(Under 37 CFR 1.47)

(65) Prior Publication Data
US 2009/0046283 A1 Feb. 19, 2009

Related U.S. Application Data

(63) Continuation-in-part of application No. 11/452,729, filed on Jun. 14, 2006.

(60) Provisional application No. 60/886,244, filed on Jan. 23, 2007, provisional application No. 60/690,385, filed on Jun. 14, 2005.

(51) Int. Cl.
*G01J 3/44* (2006.01)

(52) U.S. Cl. ........................ 356/301

(58) Field of Classification Search ........ 356/301; 438/57; 257/E21.001; 216/94
See application file for complete search history.

(56) References Cited

U.S. PATENT DOCUMENTS

| 4,965,430 | A | 10/1990 | Curtis et al. |
| 5,534,068 | A | 7/1996 | Beach et al. |
| 5,538,674 | A | 7/1996 | Nisper et al. |
| 5,557,409 | A | 9/1996 | Downer et al. |
| 6,376,177 | B1 | 4/2002 | Poponin |
| 6,406,777 | B1 | 6/2002 | Boss et al. |
| 7,057,256 | B2 | 6/2006 | Carey, III et al. |
| 7,354,792 | B2 | 4/2008 | Carey, III et al. |
| 2002/0149769 | A1 | 10/2002 | Roorda et al. |
| 2003/0029495 | A1 | 2/2003 | Mazur et al. |
| 2003/0059820 | A1 | 3/2003 | Vo-Dinh |

(Continued)

FOREIGN PATENT DOCUMENTS

DE  202004008333  8/2004

(Continued)

OTHER PUBLICATIONS

International Search Report and Written Opinion dated Aug. 14, 2008 for PCT/US2008/051643.

(Continued)

*Primary Examiner*—Tarifur Chowdhury
*Assistant Examiner*—Abdullahi Nur
(74) *Attorney, Agent, or Firm*—Thomas J. Engellenner; Reza Mollaaghababa; Nutter McClennen & Fish LLP (57) ABSTRACT

In one aspect, the present invention generally provides methods for fabricating substrates for use in a variety of analytical and/or diagnostic applications. Such a substrate can be generated by exposing a semiconductor surface (e.g., silicon surface) to a plurality of short laser pulses to generate micron-sized, and preferably submicron-sized, structures on the surface. The structured surface can then be coated with a thin metallic layer, e.g., one having a thickness in a range of about 10 nm to about 1000 nm.

9 Claims, 5 Drawing Sheets

U.S. PATENT DOCUMENTS

| | | | |
|---|---|---|---|
| 2003/0213715 | A1 | 11/2003 | Klepac et al. |
| 2004/0101469 | A1 | 5/2004 | Demers |
| 2004/0150818 | A1 | 8/2004 | Armstrong et al. |
| 2004/0162554 | A1 | 8/2004 | Lee et al. |
| 2004/0163758 | A1 | 8/2004 | Kagan et al. |
| 2005/0112544 | A1 | 5/2005 | Xu et al. |
| 2006/0038990 | A1 | 2/2006 | Habib et al. |
| 2006/0079062 | A1 | 4/2006 | Mazur et al. |
| 2006/0158653 | A1 | 7/2006 | Chiarello et al. |
| 2006/0209413 | A1* | 9/2006 | Kim et al. ............... 359/577 |
| 2006/0246573 | A1 | 11/2006 | Kurane et al. |
| 2007/0115469 | A1 | 5/2007 | Ebstein |
| 2009/0033929 | A1 | 2/2009 | Mazur et al. |

FOREIGN PATENT DOCUMENTS

| | | |
|---|---|---|
| EP | 1382459 | 1/2004 |
| EP | 1416325 | 5/2004 |
| EP | 1731962 | 12/2006 |
| WO | WO-02077608 | 10/2002 |
| WO | WO-2006060734 | 6/2006 |
| WO | WO-2006086014 | 8/2006 |
| WO | WO-2006138442 | 12/2006 |
| WO | WO-2007060989 | 5/2007 |
| WO | WO-2008091852 | 7/2008 |
| WO | WO-2008091858 | 7/2008 |

OTHER PUBLICATIONS

International Search Report and Written Opinion dated Aug. 14, 2008 for PCT/US2008/051647.

Ru, et al., "Surface Enhanced Raman Scattering Enhancement Factors: A Comprehensive Study," J. Phys. Chem. C. 2007, 111, 13794-13803.

Vo-Dinh, Surface-Ehanced Rama Spectrometry With Silver Particles on Stochasitc-Post Substrates, Analytica Chimica Acta, 1986, 139-148, vol. 181.

Vo-Dinh et al., Plasmonics-Based Nanostructures for Surface-Enhanced Raman Scattering Bioanalysis, Methods in Molecular Biology, 2005, 255-283, vol. 300.

Henley et al., Excimer laser nanostructuring of nickel thin films for the catalytic growth of carbon nanotubes, Applied Physics Letters, 2004, 4035, 84.

Henley et al., Laser-Nanostructured Ag Films as Substrates for Surface-Enhanced Raman Spectroscopy, Applied Physics Letters, 2006, 081904, 88.

Lehmann, et al., Fabrication of submicron crossed square wave gratings by dry etching and thermoplastic replication techniques, Journal of Vacuum Science Technology, Oct.-Dec. 1983, pp. 1207-1210, vol. 1, No. 4.

Nie et al., Probing Single Molecules and Single Nanoparticles by Surface-Enhanced Raman Scattering, Science Feb. 21, 1997, pp. 1102-1106, vol. 275.

Campion, et al., Surface-enhanced Raman scattering, Chemical Society Reviews, 1998, pp. 241-250, vol. 27.

Kneipp, et al., Ultrasenstive Chemical Analysis by Raman Spectroscopy, Chemical Review, 1999, pp. 2957-2975, vol. 99.

Emory, et al., Direct Observation of Size-Dependent Optical Enhancement in Single Metal Nanoparticles, Journal of American Chemical Society, 1998, pp. 8009-8010, vol. 120.

Kottmann, et al., Plasmon resonant coupling in metallic nanowires, Optics Express, Jun. 4, 2001, pp. 655-663, vol. 8, issue 12.

Jiang, et al., Single Molecule Raman Spectroscopy at the Junctions of Large Ag Nanocrystals, Journal of Physical Chemistry, 2003, pp. 9964-9972, vol. 107.

Genov, et al., Resonant Field Enhancements from Metal Nanoparticle Arrays, Nano Letters, 2004, pp. 153-158, vol. 4, issue 1.

Cao, et al., Nanoparticles with Raman Spectroscopic Fingerprints for DNA and RNA Detection, Science, Aug. 30, 2002, pp. 1536-1340, vol. 297.

Liu, et al., Nanopillar Substrates for SERS, Proceedings of the 7th International Conf. on Miniaturized Chemical and Biochemical Analysis Systems, Oct. 5-9, 2003, pp. 705-708.

Liu, et al., Cinfigurable 3D Nanoscale High Aspect Ratio Pillars for Surface-Enhanced Raman Spectroscopy IEEE 2003, pp. 425-427.

Liu et al., Nanowell surface enhanced Raman scattering arrays fabricated by soft-lithography for label-free biomolecular detections in integrated microfluidics, Applied Physics Letters, 2005, pp. 074101-1-074101-3, vol. 87.

Duyne, et al., Atomic force microscopy and surface-enhanced Raman spectroscopy I. Ag island films and Ag film over polymer nanosphere surfaces supported on glass, Journal of Chemical Physics, Aug. 1, 1993, pp. 2101-2115, vol. 99, issue 3.

Quagliano, The SERS Effect as a Tool for Studying Molecules Absorbed on Semiconductor Surfaces, The Internet Journal of Vibrational Spectroscopy, 2004, vol. 4, Edition 2.

Drachev, et al., Adaptive silver films towards bio-array applications.

Haynes, et al., Nanosphere Lithography: A Versatile Nanofabrication Tool for Studies of Size-Dependent Nanoparticle Optics, Journal of Physical Chemistry, 2001, pp. 5599-5611, vol. 105, Issue 24.

Zhang, et al., An electrochemical surface-enhanced Raman spectroscopy approach to anthrax detection, Proc. of SPIE, vol. 5221, pp. 82-91.

Drachev, et al., Adaptive Silver Films for Detection of Antibody-Antigen Binding, 2005, pp. 8368-8373, vol. 21, Issue 18.

Lyandres, et al., Real-Time Glucose Sensing by Surface-Enhanced Raman Spectroscopy in Bovine Plasma Facilitated by a Mixed Decanethiol/Mercaptohexanol Partition Layer, Analytical Chemistry, Oct. 1, 2005, pp. 6134-6139, vol. 77, Issue 19.

Fagano, et al., Raman Spectroscopic Study of the Avidin-Biotin Complex, Journal of Raman Spectroscopy, 1995, pp. 991-995, vol. 26.

Duyne, et al., Spatially Resolved Surface Enhanced Raman Spectroscopy: Feasibility, Intensity Dependence on Sampling Area and Attomole Mass Sensitivity, May 2, 1986, pp. 190-196, vol. 126, issue 2.

Drachev, et al, Surface-Enhanced Raman Difference between Human Insulin and Insulin Lispro Detected with Adaptive Nanostructures, Journal of Physical Chemistry, 2004, pp. 18046-18052, vol. 108.

Kneipp, et al., Single Molecule Detection Using Surface-Enhanced Raman Scattering (SERS), Physical Review Letters, Mar. 3, 1997, pp. 1667-1670, vol. 78, issue 9.

Haynes, et al., Plasmon Scanned Surface-Enhanced Raman Scattering Excitation Profiles, Materials Research Society Symposia Proceedings, 2002, p. 7.1-7.6, vol. 728.

Her, et al., Femtosecond laser-induced formation of spikes on silicon, Applied Physicals A. Materials Science & Processing, 2000, pp. 383-385, vol. 70.

Shen, et al., Femtosecond laser-induced formation of submicrometer spikes on silicon in water, Applied Physicals Letters, Dec. 6, 2004, pp. 5694-5696, vol. 85, issue 23.

Shen, et al., Formation of regular arrays of siliconmicrospikes by femtosecond laser irradiation through a mask, Applied Physics Letters, pp. 1715-1717, vol. 82, issue 11.

Laibinis, et al., Comparison of the Structures and Wetting Properties of Self-Assembled Monolayers of n-Alkanethiols on the Coinage Metal Surfaces, Cu, Ag, Au, Journal of the American Chemical Society, 1991, pp. 7152-7167, vol. 113.

Sockalingum, et al., Raman and SERS spectroscopy for probing drug-target interactions: from in-vitro models to intracellular imaging, Internet Journal of Vibrational Spectroscopy.

Astilean, et al., Ordered Metallic Nanostructures for Surface-Enhanced Raman Spectroscopy, Romanian Reports in Physics, 2004, pp. 346-351, vol. 56, issue 3.

Bergman, et al., Relationship between surface-enhanced Raman scattering and the dielectric properties of aggregared silver films, Optics Letters, Jan. 1981, pp. 33-35, vol. 6, issue 1.

Katayama, et al., Formation of ring patterns surrounded by ripples by single-shot laser irradiation with ultrashort pulse width at the solid/liquid interface, Applied Physics Letters, Jun. 16, 2003, pp. 4244-4246, vol. 82, No. 24.

Sylvia, et al., Surface-Enhanced Raman Detection of 2,4-Dinitrotoleune Impurity Vapor as a Marker To Locate Landmines, Analytical Chemistry, Dec. 1, 2000, pp. 5834, 5840, vol. 72.

Quagilano, et al., The SERS Effect as a Tool for Studying Molecules Adsorbed on Semiconductor Surfaces, The Internet Journal of Vibrational Spectroscopy, vol. 4, Ed. 2 (2004).

Keller S, et al., "Quality control of food with near-infrared-excited Raman spectroscopy" Fresenius Journal of Analytical Chemistry, vol. 346, Jun. 1993, pp. 863-867.

Montoya, et al., "Detection of Salmonella using Surfaced Enhanced Raman Scattering" Chemical and Biological Sensing IV, Proceedings of SPIE, vol. 5085, Apr. 21, 2003, pp. 144-152.

Liu, et al., "Nanowell surface enhanced Raman scattering arrays fabricated by soft-lithography for label-free biomolecular detections in integrated microfluidics," 2005 American Institute of Physics, Applied Physics Letters 87 (3 pages), 2005.

Stuart, et al., "Biological applications of localised surface plasmonic phenomenae", 20050201; 20050200, vol. 152, No. 1, pp. 13-32, XP006023676, 2005.

Jung, et al., "Facile fabrication of large area nanostructures for efficient surface-enhanced Raman scattering," J. Mater. Chem., 2006, 16, 3145-3149.

Kneipp, et al., "Population Pumping of Excited Vibrational States by Spontaneous Surface-Enhanced Raman Scattering," The American Physical Society, Physical Review Letters, vol. 76, No. 14, Apr. 1, 1996, pp. 2444-2447.

Ihlemann, J. et al., "Excimer Laser Micro Machining of Inorganic Dielectrics" Applied Surface Science, Elsevier, Amsterdam, NL, vol. 106, Oct. 1, 1996, pp. 282-286, XP000879307 ISSN: 0169-4332.

Xia, Q. et al., "Ultrafest Patterning of Nanostructures in Polymers Using Laser Assisted Nanoimprint Lithography" Applied Physics Letters, AIP, American Institute of Physics, Melville, NY, vol. 83, No. 21, Nov. 24, 2003, pp. 4417-4419, XP001191757, ISSN: 003-6951.

* cited by examiner

METALIZED SEMICONDUCTOR SUBSTRATES FOR RAMAN SPECTROSCOPY

RELATED APPLICATION

This application claims priority to a provisional application entitled "Metalized Semiconductor Substrates for Raman Spectroscopy," which was filed on Jan. 23, 2007 and has a Ser. No. 60/886,244.

This application is also a continuation-in-part (CIP) of U.S. patent application entitled "Applications of Laser-Processed Substrate for Molecular Diagnostics," filed on Jun. 14, 2006 having a Ser. No. 11/452,729, which in turn claims priority to a provisional application filed on Jun. 14, 2005 and having a Ser. No. 60/690,385.

BACKGROUND

The present invention relates generally to methods for fabricating substrates suitable for use in analytical and diagnostic optical systems, and in particular, substrates for use in Raman spectroscopy.

Raman spectroscopy can be employed as an analytical as well as a diagnostic technique in a variety of applications, such as material characterization and identification. It relies on inelastic scattering of incident photons by a molecule, via coupling to its vibrational modes, to provide an essentially unique signature for that molecule. In particular, such inelastic scattering (commonly known as Raman scattering) can cause a decrease or an increase in the scattered photon energy, which appear as "Stokes" and "anti-Stokes" peaks in a wavelength-dispersed spectrum of the scattered photons. A drawback of Raman spectroscopy is the relatively few incidences of such inelastic scattering. The probability that a scattering event will occur is typically called "cross-section," which is expressed in terms of area.

Raman scattering cross-sections can, however, be significantly enhanced by placing the molecule on or near a conductive surface. Such a mode of performing Raman spectroscopy is commonly known as surface enhanced Raman spectroscopy (SERS). Although SERS is a promising technique for extending the use of Raman spectroscopy to a variety of new applications, its use is currently limited due to a dearth of reliable, high performance substrates.

Accordingly, there is a need for substrates for use in SERS, as well as other applications, that can provide a high degree of reliability and performance. There is also a need for methods of fabricating such substrates with a high degree of reproducibility, which can be easily and, preferably inexpensively, implemented.

SUMMARY

In one aspect, a method of fabricating a substrate suitable for use in a variety of applications, such as surface enhanced Raman spectroscopy, is disclosed. The method includes generating micron-sized, and preferably submicron-sized structures, on a substrate surface, e.g., a semiconductor surface such as a silicon surface, by exposing the surface to a plurality of short laser pulses, e.g., sub-picosecond pulses (e.g., pulses having durations in a range of about 100 femtoseconds ($10^{-15}$ seconds) to about one picosecond ($10^{-12}$ seconds)). In many cases, the pulses are applied to the surface while the surface is in contact with a liquid, e.g., polar or a non-polar liquid. Subsequently, the structured surface is coated with a thin metallic layer (e.g., a metallic layer having a thickness in a range of about 10 nm to about 1000 nm, and preferably in a range of about 50 nm to about 120 nm). In many cases, the metallic layer exhibits micron-sized, and preferably sub-micron-sized, structures that correspond substantially to the structures present in the underlying surface.

In another aspect, a diagnostic method is disclosed that includes generating a plurality of micron-sized and/or submicron-sized structures on a substrate surface, e.g., a semiconductor surface, by exposing the surface to a plurality of short laser pulses, followed by disposing a metallic layer, e.g., one having a thickness in a range of about 10 nm to about 1000 nm (and preferably in a range of about 50 nm to about 120 nm), over the structured surface. The metal-covered surface, which can exhibit structures corresponding substantially to the structures present on the underlying substrate surface, can then be utilized as a substrate for a diagnostic assay. In some cases, the diagnostic assay can comprise performing surface enhanced Raman spectroscopy.

In other aspect, a substrate for use in Raman spectroscopy, and other analytical and/or diagnostic applications, is disclosed that includes a substrate, e.g., a semiconductor substrate such as a silicon wafer, having a surface that exhibits micron-sized, and preferably sized, submicron-structures. A metallic layer having a thickness in a range of about 10 nm to about 1000 nm, and preferably in a range of about 50 nm to about 120 nm, covers at least a portion of the structured semiconductor surface. The metallic layer exhibits micronssized, and preferably submicron-sized, structures (surface undulations). In many cases, the structured of the metallic layer correspond substantially to the structures present on the semiconductor surface.

Further understanding of the invention can be obtained by reference to the following detailed description in conjunction with the associated drawings, which are briefly described below.

DETAILED DESCRIPTION

The present invention generally provides sensing substrates that are suitable for use in a variety of applications, including surface enhanced Raman spectroscopy (SERS). In some embodiments, a surface of a semiconductor substrate, e.g., silicon, is exposed to a plurality of short laser pulses (e.g., sub-picosecond laser pulses) to generate micron-sized, and preferably submicron-sized, structures (e.g., in the form of spikes) on that surface. The structured surface can then be coated with a thin layer of a metal, e.g., silver or gold, to be used as a substrate for SERS, or other applications. The term "structured surface," as used herein, refers to a surface that exhibits undulations (e.g., spikes) with peak-to-trough excursions (e.g., amplitudes) of a few microns (e.g., less than about 20 microns), and preferably less than about 1 microns, and more preferably less than about 100 nanometer (e.g., in a range of about 1 nm to about 50 nm). The "structured surface" can exhibit a surface roughness with amplitudes less than about 1 micron, and preferably less than about 100 nanometers, and more preferably less than about 50 nm.

Figure 1:
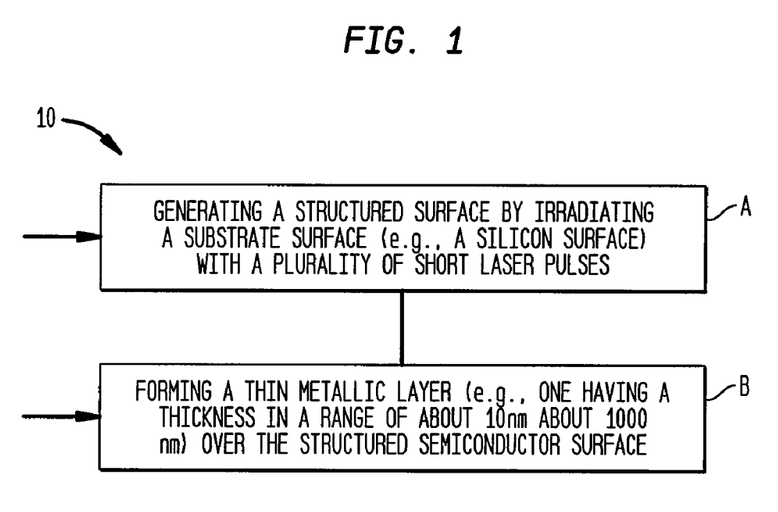
FIG. 1 is a flow chart depicting various steps in some exemplary embodiments of methods of the invention for generating a metalized semiconductor sensing substrate, FIG. 2 schematically depicts an exemplary apparatus suitable for generating micron-sized or submicron-sized structures on a substrates' surface, such as a semiconductor surface.

With reference to a flow chart 10 shown in FIG. 1, an exemplary method in accordance with one embodiment of the invention for fabricating a metalized sensing substrate, e.g., one suitable for use in surface enhanced Raman spectroscopy (SERS), comprises generating a structured surface (step A) by irradiating a substrate surface (e.g., a semiconductor surface, such as a silicon surface) with a plurality of short laser pulses. The term "short laser pulses," as used herein, refers to laser pulses having durations less than about a few nanoseconds ($10^{-9}$ seconds), e.g., pulses with durations in a range of about 100 femtoseconds ($10^{-15}$ seconds) to about one picosecond ($10^{-12}$ seconds). By way of example, in some embodiments, a silicon substrate can be exposed to a plurality of short pulses (e.g., pulses having durations in a range of about 100 femtoseconds to about 500 femtoseconds) while the surface is in contact with a fluid, e.g., water. The pulses cause a change in surface topography characterized by surface undulations (e.g., surface roughness) having amplitudes less than about a few microns (e.g., less than about 10 microns), and preferably less than about 1 micron, e.g., in a range of about 50 nm to about 200 nanometers.

Figure 2:
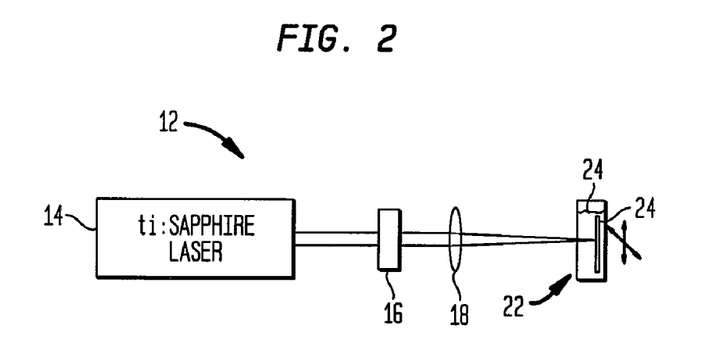

By way of example, FIG. 2 schematically depicts an exemplary optical system 12 suitable for processing a substrate (e.g., a semiconductor substrate) so as to generate micron-sized, and preferably submicron-sized, features (structures) on a surface thereof. For example, the features can include a plurality of spikes, e.g., substantially columnar structures extending from the surface to a height above the surface. The optical system 12 includes a Titanium-Sapphire (Ti:Sapphire) laser 14 for generating short laser pulses. By way of example, the Ti:Sapphire laser can generate laser pulses with a pulse width of about 80 femtoseconds at 800 nm wavelength (e.g., at an average power of 300 mW and at a repetition rate of 95 MHz). The pulses generated by the Ti:Sapphire laser can be applied to a chirped-pulse regenerative amplifier (not shown) that, in turn, can produce, e.g., 0.4 millijoule (mJ)), 100 femtosecond pulses at a wavelength of 800 nm and at a repetition rate of about 1 kilohertz.

The optical system 12 further includes a harmonic generation system 16 that receives the amplified pulses and doubles their frequency to produce, e.g., 100-femtosecond second-harmonic pulses at a wavelength of 400 nanometers. A lens 18 focuses the second-harmonic pulses onto a surface of a semiconductor sample 20, which can be disposed on a three-dimensional translation system (not shown). A glass liquid cell 22 can be coupled to the semiconductor sample so as to allow the sample surface exposed to the pulses to have contact with a liquid 24 (e.g., water) contained within the cell. Further details regarding methods and apparatuses for generating micron-sized, and preferably submicron-sized, features on a semiconductor surface can be found in co-pending U.S. patent application entitled "Femtosecond Laser-Induced Formation Of Submicrometer Spikes On A Semiconductor Substrate" having a Ser. No. 11/196,929, filed Aug. 4, 2005, which is herein incorporated by reference. U.S. Pat. No. 7,057,256 entitled "Silicon-Based Visible And Near-Infrared Optoelectronic Devices" and Published U.S. Patent Application No. 2003/00299495 entitled "Systems And Methods For Light Absorption and Field Emission Using Microstructured Silicon," both of which are herein incorporated by reference, provide further disclosures regarding microstructuring silicon surfaces by application of short laser pulses.

Figure 3:
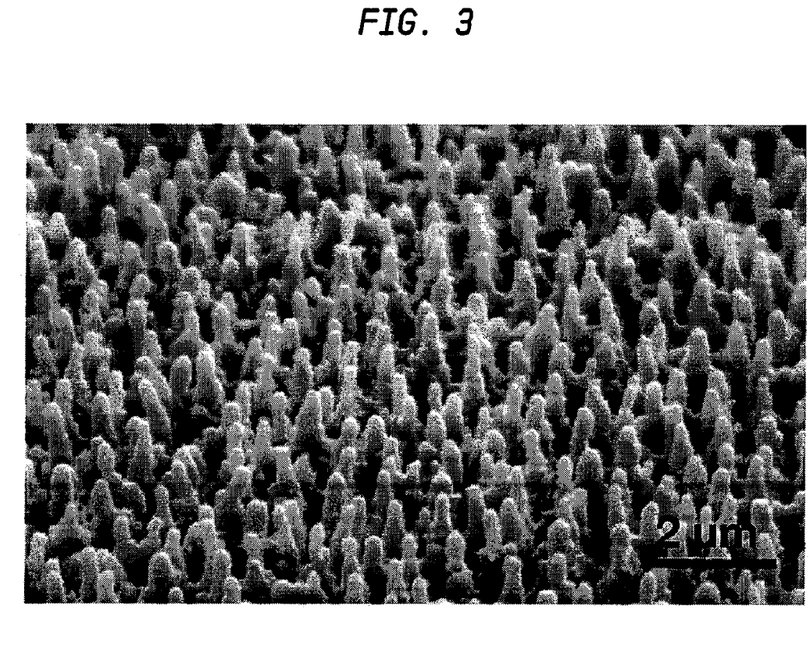
FIG. 3 shows nanosized structures, in the form of spikes, formed on a silicon surface by exposing the surface to a plurality of femtosecond pulses while the surface is in contact with water, FIG. 4 schematically depicts a sensing substrate according to an embodiment of the invention, which includes a structured semiconductor surface coated with a thin metallic layer, and its use in SERS.

By way of illustration, FIG. 3 shows a silicon surface on which a plurality of nanosized features are generated via irradiation of the surface with a plurality of femtosecond laser pulses while the surface was in contact with water.

Referring again to the flow chart 10 of FIG. 1, in step (B), the structured semiconductor surface can be coated with a thin metallic layer, e.g., silver or gold, to generate a substrate for use in surface enhanced Raman spectroscopy (SERS), or other applications. The metallic layer exhibits a thickness in a range of about 10 nm to about 1000 nm, and more preferably in a range of about 50 nm to about 120 nm. In many embodiments, the metallic layer exhibits micron-sized, and preferably submicron-sized, features (structures) that substantially correspond to those of the underlying semiconductor surface. The metallic coating (e.g., a coating of Au, Ag, Pt, Rh, or other suitable metals) can be formed over the structured semiconductor surface, e.g., via evaporation, sputtering, electroplating or other suitable metal deposition methods. In this manner, a conductive surface exhibiting micron-sized, and preferably submicron-sized structures, can be formed that can be utilized in a variety of analytical and/or diagnostic applications, such as Raman spectroscopy.

The metal coating, which in many embodiments has a thickness comparable to, or smaller than, the wavelength of visible light, can provide an electric field enhancing conductive surface. Without being limited to any particular theory, the metal surface can exhibit surface plasmon resonance effects that can enhance electric fields in the vicinity of its mesostructures. Such enhancement of the electric field in the vicinity of the surface can advantageously be utilized in a variety of applications, such as Raman spectroscopy.

Figure 4:
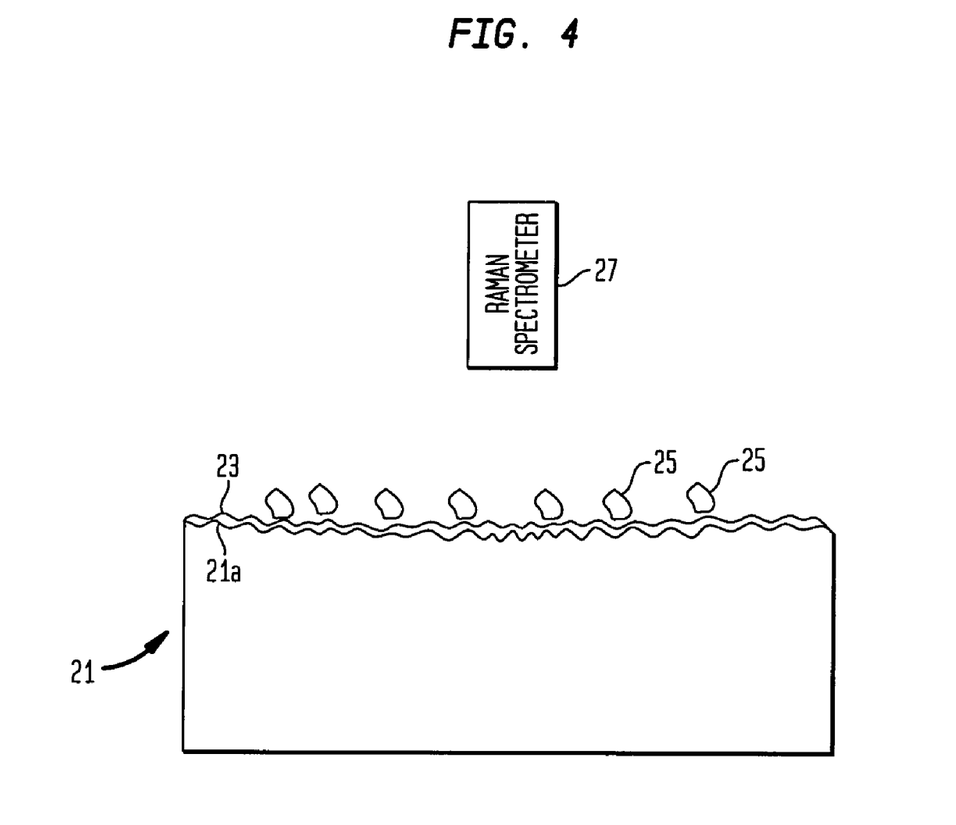

By way of example, FIG. 4 schematically depicts a silicon substrate 21 having a structured surface 21a (a surface exhibiting micron-sized or preferably submicron-sized structures) on which a thin metal layer 23 (e.g., a metal layer having a thickness in a range of about 10 nm to about 1000 nm, and preferably in a range of about 50 nm to about 120 nm) is deposited. The structured silicon surface can be formed in a manner discussed above (by exposure to short laser pulses), and the metal layer can be formed over the surface by any suitable method, such as evaporation and electrodeposition. In some embodiments, the metal-covered surface can be utilized as a sensing substrate for performing SERS. For example, an analyte of interest 25 can be disposed over the surface, or in proximity of the surface, and its Raman spectrum can be obtained by utilizing a Raman spectrometer 27. In other cases, the substrate surface can be placed within an environment so as to be in contact with, or in proximity of, one or more molecular species in that environment. The Raman spectra of those species can then be measured so as to obtain information about the environment, e.g., the presence and/or quantity of one or more analytes (molecular species).

The applications of the sensing substrates of the invention are not limited to those discussed above. For example, the metalized polymeric substrates of the invention can find a variety of uses in areas that require intense optical fields at a surface.

The following example provides further illustration of the salient aspects of the invention, and is provided only for illustrative purposes and to show the efficacy of the methods and systems according to the invention for significantly enhancing the signal-to-noise ratio in SERS. The example, however, does not necessarily show the optimal results (e.g., optimal signal-to-noise ratios) that can be obtained by employing the substrates of the invention.

EXAMPLE

Figure 5A:
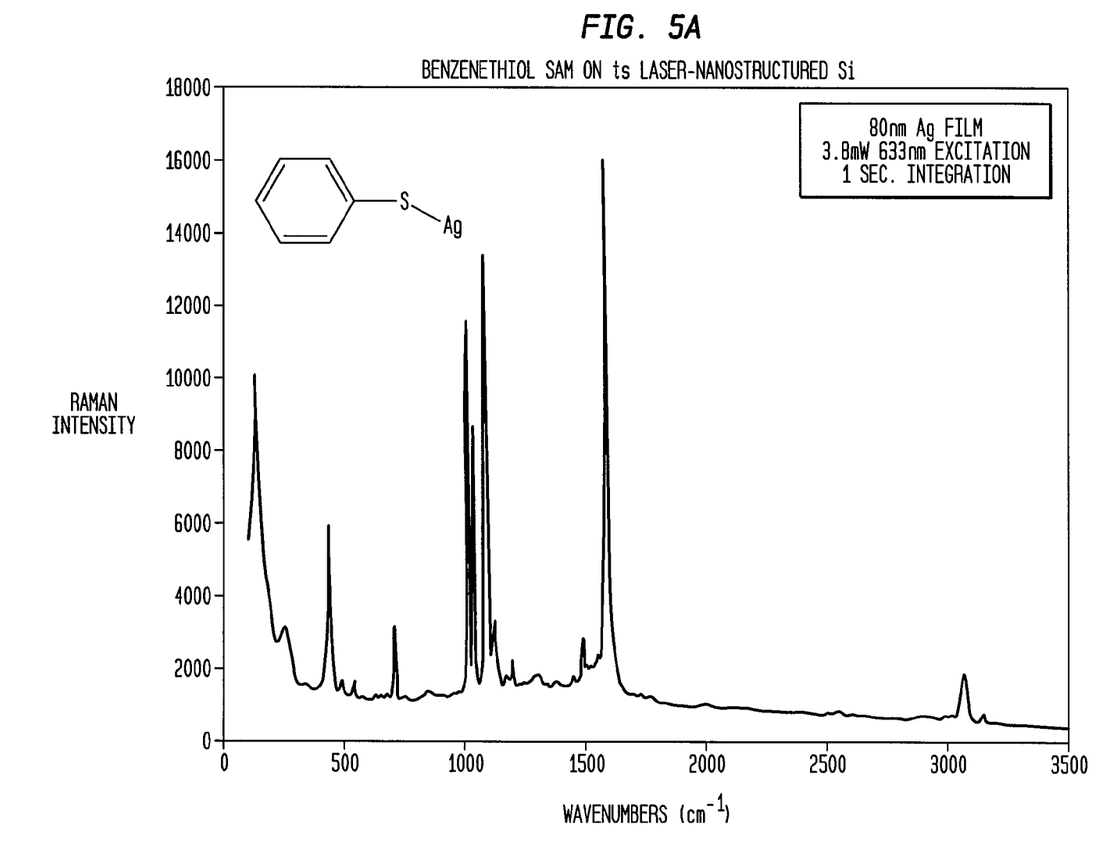
FIG. 5A is a surface enhanced Raman spectrum of a film of Benzenethiol disposed over a metal-covered structured silicon surface.
Figure 5B:
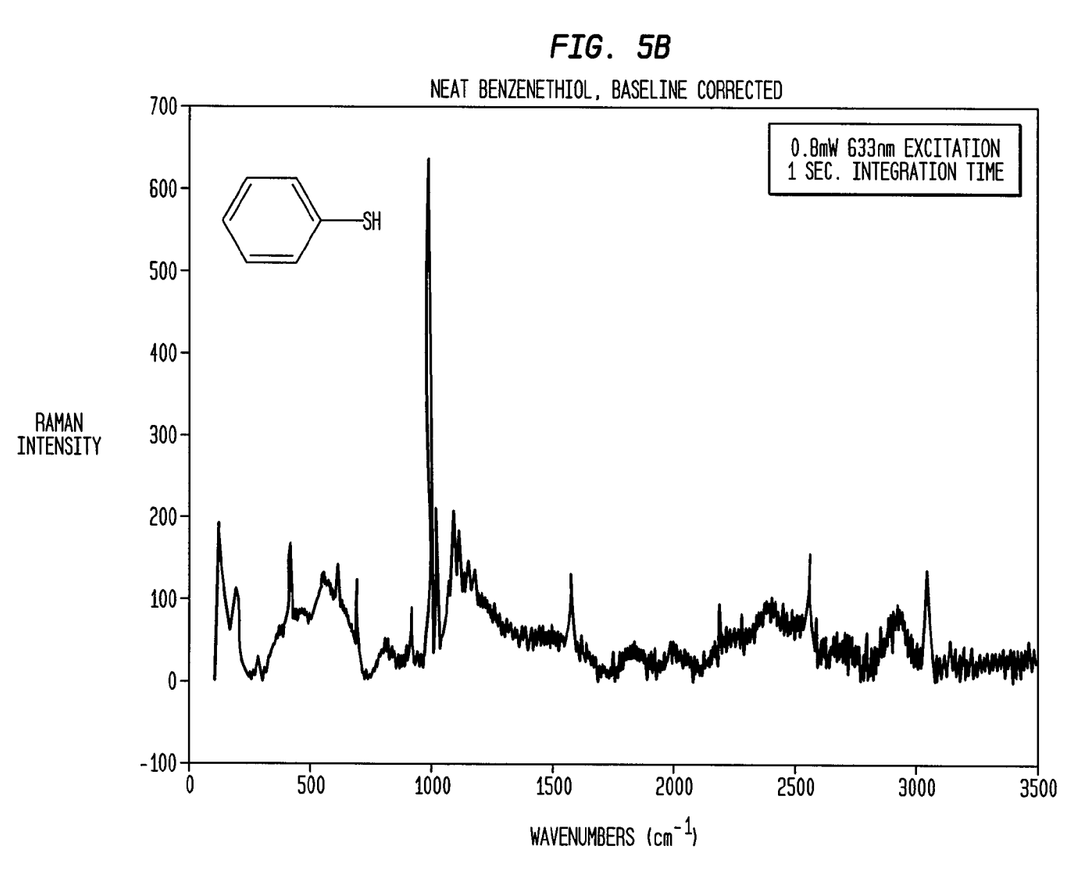
FIG. 5B is a control Raman spectrum of neat, bulk Benzenethiol.

A silicon surface was irradiated with a plurality of femtosecond laser pulses with a pulse width of about 100 femtoseconds while the surface was in contact with water such that each surface location was exposed to about 500 laser pulses. In this manner, a plurality of submicron-sized features were formed on the silicon surface. A thin layer of silver with a thickness of about 80 nm was deposited over the nanostructured silicon surface. A film of Benzenethiol was disposed on the metal-covered surface and a Raman spectrum of the Benzenethiol was obtained by employing a commercial Raman spectrometer manufactured by Horiba Jobin Yvon, Inc. of New Jersey, U.S.A., under the trade designation Aramis. This Raman spectrum is shown in FIG. 5A. As a control, the Raman spectrum of bulk, neat Benzenethiol was obtained by employing the same spectrometer. The control spectrum is shown in FIG. 5B. A comparison of the spectra presented in FIGS. 5A and 5B indicates that the use of the metal-covered nanostructured silicon surface results in an enhancement of the order of $10^{10}$ in the signal-to-noise ratio of the Raman spectrum.

A self-assembled monolayer (SAM) of benzenethiol can be used to quantify the number of molecules present on the structured surfaces. The molecular packing density of benzenethiol on a silver surface is known to be approximately $4 \times 10^{14}$ cm$^{-2}$. For the Raman spectra of the SAM on a silver coated structured semiconductor surface, the integrated peak intensity of a single Raman band can be normalized with a Raman band from the spectrum of a sample of neat benzenethiol so as to derive an enhancement factor of the scattering cross section per individual molecule. With knowledge of the neat sample's refractive index, molar volume, and probed volume, the EF of the various substrates can be determined. Utilizing this approach, in one set of experiments, an enhancement factor (EF) of about $1.88 \times 10^{10}$ for the 1000 cm$^{-1}$ band, and an EF of about $1.49 \times 10^{11}$ for the 1572 cm$^{-1}$ band of Benzenethiol was obtained by utilizing a silver-coated structured silicon surfaces.

It should be understood that the enhancement factor can be defined differently than that discussed above, which can lead to different numerical values for the enhancement factor. Regardless, the above exemplary data shows that a significant enhancement factor can be achieved by the use of the metalized structured substrate. By way of example, an article entitled "Surface Enhanced Raman Scattering Enhancement Factors: A Comprehensive Study," authored by Le Ru et al. and published in J. Phys. Chem. C 2007, 111, 13794-13803 describes various definitions of SERS enhancement factors. This article in herein incorporated by reference in its entirety.

Those having ordinary skill in the art will appreciate that various modifications can be made to the above embodiments without departing from the scope of the invention.

What is claimed is:

1. A method of fabricating a sensing substrate, comprising
    exposing a semiconductor surface to a plurality of short laser pulses to generate a plurality of micron-sized and/or submicron-sized structures therein,
    disposing a metallic layer over said structured semiconductor surface,
    wherein said metallic layer has a thickness in a range of about 10 nm to about 1000 nm; wherein said short pulses have a pulse duration in a range of about 100 femtoseconds to about tens of nanoseconds.

2. The method of claim 1, wherein said metallic layer has a thickness in a range of about 50 nm to about 120 nm.

3. The method of claim 1, further comprising selecting said short pulses to have durations in a range of about 100 femtoseconds to about one picosecond.

4. The method of claim 1, wherein said structures comprise a plurality of surface undulations having amplitudes less than about 1 micron.

5. A diagnostic method, comprising
    generating a plurality of micron-sized and/or submicron-sized structures on a substrate surface by exposing the surface to a plurality of short laser pulses,
    depositing a metallic layer over said structured surface,
    utilizing said metal-covered surface as a substrate for a diagnostic assay; wherein said short pulses have a pulse duration in a range of about 100 femtoseconds to about tens of nanoseconds.

6. The diagnostic method of claim 5, wherein said metallic layer has a thickness in a rang of about 10 nm to about 1000 nm.

7. The diagnostic method of claim 5, wherein said metal layer exhibits structures substantially corresponding to structures present on the underlying substrate surface.

8. The diagnostic method of claim 5, wherein said substrate comprises a semiconductor substrate.

9. The diagnostic method of claim 8, wherein said diagnostic assay comprises performing surface enhanced Raman spectroscopy.

* * * * *